(12) United States Patent
Adell

(10) Patent No.: US 9,597,221 B1
(45) Date of Patent: Mar. 21, 2017

(54) MATERIALS AND METHODS FOR FABRICATING A DENTAL ARCH APPLIANCE COMPRISING SILICONE

(71) Applicant: Loren S. Adell, Sunnyvale, CA (US)

(72) Inventor: Loren S. Adell, Sunnyvale, CA (US)

(73) Assignees: Loren S. Adell, Sunnyvale, TX (US); Michael Adell, Sunnyvale, TX (US)

( * ) Notice: Subject to any disclaimer, the term of this patent is extended or adjusted under 35 U.S.C. 154(b) by 0 days.

(21) Appl. No.: 14/099,067

(22) Filed: Dec. 6, 2013

(51) Int. Cl.
- *A61C 5/00* (2006.01)
- *A61F 5/56* (2006.01)
- *A63B 71/08* (2006.01)
- *A61C 7/36* (2006.01)
- *A63C 7/08* (2006.01)

(52) U.S. Cl.
CPC ............ *A61F 5/566* (2013.01); *A63B 71/085* (2013.01); *A61C 7/36* (2013.01); *A61F 5/56* (2013.01); *A61F 2005/563* (2013.01); *A63C 7/08* (2013.01)

(58) Field of Classification Search
CPC .. A63B 71/085; A61F 5/566; A61F 2005/563; A61F 5/56; A61C 7/08; A61C 9/0006; A61C 7/36
USPC .................... 264/16; 428/35.7; 128/861, 862
See application file for complete search history.

(56) References Cited

U.S. PATENT DOCUMENTS

| | | | | |
|---|---|---|---|---|
| 3,303,844 A * | 2/1967 | Johnson et al. | ............... | 128/862 |
| 4,063,552 A * | 12/1977 | Going et al. | ................... | 128/861 |
| 5,371,162 A * | 12/1994 | Konings et al. | ................ | 528/15 |
| 2006/0130851 A1 * | 6/2006 | Mathias | ........................ | 128/861 |
| 2009/0221884 A1 * | 9/2009 | Ryan | ............................. | 600/301 |

* cited by examiner

Primary Examiner — Robert J Grun
(74) Attorney, Agent, or Firm — George L. Boller

(57) ABSTRACT

A pre-packaged mixture of uncured silicone and a hibernating catalyst, either a tin-based catalyst or a platinum-based catalyst, is shipped from a manufacturer to an end user for use in fabricating a silicone dental arch appliance.

9 Claims, 5 Drawing Sheets

MATERIALS AND METHODS FOR FABRICATING A DENTAL ARCH APPLIANCE COMPRISING SILICONE

TECHNICAL FIELD

This invention relates to dental arch appliances, especially ones which use silicone for fitting over teeth of a person's dental arch. The invention concerns materials and methods for fabricating such appliances.

BACKGROUND

There are various types of dental arch appliances which comprise silicone for fitting an appliance over teeth of a person's dental arch. Certain appliances may have particular constructional features and/or include one or more non-silicone elements in their construction for enabling a particular appliance to perform a particular function.

Two examples of such appliances are mouth guards and snore guards. A mouth guard is worn by a person to protect his/her teeth against injury from an external source or from his/her own tooth grinding. A snore guard is worn when a person is sleeping to prevent snoring. Other appliances are used for dental procedures.

One type of mouth guard is a pre-formed, non-adjustable one which, although slightly resiliently compressible, cannot be reshaped by the user to achieve precise conformance to the user's individual teeth. Pre-formed mouth guards are typically fabricated as a commodity product by injection molding a thermoset plastic material in a mold cavity.

Another type of mouth guard, sometimes called a "boil and bite" mouth guard, can enable the user to achieve a better fit than with the pre-formed, non-adjustable type because it is manufactured by molding thermoset plastic in a mold cavity. As manufactured, the mouth guard has a general shape for fitting unto an arch. The user who has purchased such a mouth guard heats it in hot water to soften the thermoplastic. Once the material has cooled, but is still somewhat soft and formable, the user puts the mouth guard in the mouth and forms it around individual teeth. When fully cooled, the material retains the shape to which it has been formed by the user while retaining some resilient compressibility.

Custom-fit mouth guards are yet another type. This type precisely fits a person's dental arch and is typically fabricated in a dental office or laboratory. The fabrication process begins by taking an impression of the person's dental arch. The impression is then used to fabricate a model of the person's arch. A dentist or laboratory technician next mixes together a formable material and a catalyst for curing the formable material to create an appropriate amount of workable bulk material for forming onto the arch model. The formable material and the catalyst have respective formulations which initiate curing of the material upon mixing such that they provide a limited length of time for the dentist or technician to create an impression in the material which will capture minute features of the arch. The time may be sufficiently limited that minute features may not be captured.

As the bulk material is being worked onto the arch model by the fabricator to capture a desired impression of the arch model, the material may cure sufficiently that the outward appearance of the material cannot be further changed by the use of the same tool or tools which had heretofore been used. In that case a different tool or tools have to be used in order to achieve a desired finished appearance for the appliance. The need to use such tools, such as cutters and grinders contributes to the amount of time and labor involved in creating the final appliance.

Because of the nature of the raw materials and the amount of time and labor involved in its fabrication, a custom-made mouth guard is typically considerably more expensive than the previously mentioned types although it is certainly a better finished product.

SUMMARY OF THE INVENTION

Through the use of the presently disclosed materials and methods, Applicant enables a custom-fit silicone dental arch appliance to be fabricated without the time limitation discussed above, enabling fine detail to be captured in an impression, and with better efficiency than by a method such as the one described above.

Rather than mixing together uncured silicone and an active catalyst before working the silicone onto an arch model as described above, the dentist or laboratory technician uses uncured silicone within which a hibernating catalyst is already embedded. The two constituents are respectively formulated to keep the uncured silicone in that state so that it will not cure until the catalyst is awakened by a particular external influence. This allows the fabricator to work the uncured material onto a dental arch model to obtain not only the desired tooth impression, including minute detail when required, but also a desired outward final appearance for the appliance or at least an outward appearance which is closer to final than that which can be achieved by the known method described above. It is only then that the catalyst is awakened by application of an external environmental trigger to initiate curing of the silicone.

Uncured silicone containing a hibernating catalyst can be manufactured in either of two formulations, one for curing by a tin catalyzation process, the other for curing by a platinum catalyzation process. The external environmental triggers for the respective formulations differ and each process may have certain advantages over the other.

Curing by tin catalyzation is triggered by exposure to a moist atmosphere and can take place without external heating although a moist atmosphere may be provided by steam. Curing by platinum catalyzation occurs at elevating the temperature of the material using a heat source. With appropriate heating, the silicone can cure quickly and without generating volatile byproducts. Platinum-catalyzed silicone typically shrinks less than tin-catalyzed silicone during curing.

Because platinum-catalyzed silicone may be susceptible to "poisoning" which inhibits curing, the dental arch model onto which it will be worked needs to be free of potential inhibitors.

Uncured silicone containing a hibernating catalyst is packaged after its manufacture in a manner which is intended to avoid unintentional or inadvertent activation of the catalyst until such time as the manufactured material is ready to be used by a manufacturer's customer, such as a dentist's office or dental laboratory, who has purchased the material from the manufacturer. Tin-catalyzed silicone is packaged in a hermetically sealed enclosure which is essentially free of moisture and which prevents intrusion of moisture until opened. Platinum-catalyzed silicone may be packaged in the same way, but because its catalytic action is not triggered by moisture, the sealing provided by its packaging enclosure need not necessarily be hermetic.

One general aspect of the disclosure relates to pre-packaged uncured silicone comprising: silicone; a catalyst, comprising one of a tin-based catalyst and a platinum-based catalyst, which is hibernating within the silicone and which when awakened from hibernation by an external influence will be effective to cause the uncured silicone to begin to cure by catalytic action; and packaging which encloses the silicone.

Another general aspect of the disclosure relates to a method of fabricating a silicone dental arch appliance which fits over one of more teeth of a person's dental arch.

The method comprises: placing silicone which contains a hibernating catalyst over one or more teeth of a dental arch model of a person's dental arch and working the silicone to capture an impression of one or more teeth of the arch model in the silicone; removing unwanted silicone from worked silicone; and awakening the catalyst to cause uncured silicone remaining on the model to begin to cure by exposing the uncured silicone to an external influence which is effective on the catalyst to cause the silicone to begin to cure by catalytic action.

Another general aspect of the disclosure relates to a method of enabling a silicone dental arch appliance which fits over one or more teeth of a person's dental arch to be fabricated by an end user of a commercial product comprising a mixture of uncured silicone and a hibernating catalyst which will awaken in response to an external influence effective to cause the uncured silicone to begin curing by catalytic action.

The method comprises: manufacturing a mixture of uncured silicone and a hibernating catalyst; after manufacture of the mixture, enclosing the mixture within a sealed enclosure to create a commercial product; then shipping the commercial product from the manufacturer to an end user; then, at the end user, opening the enclosure, removing the mixture, and working the mixture onto a dental arch model of a person's dental arch to capture in the worked mixture an impression of one or more teeth of the dental arch model; removing unwanted mixture from the worked mixture while leaving the impression; and exposing the dental arch model with the unremoved mixture on it to an external influence which is effective to awaken the catalyst and cause the silicone to begin to cure by catalytic action.

The foregoing summary, accompanied by further detail of the disclosure, will be presented in the Detailed Description below with reference to the following drawings that are part of this disclosure.

DETAILED DESCRIPTION

Figure 1:
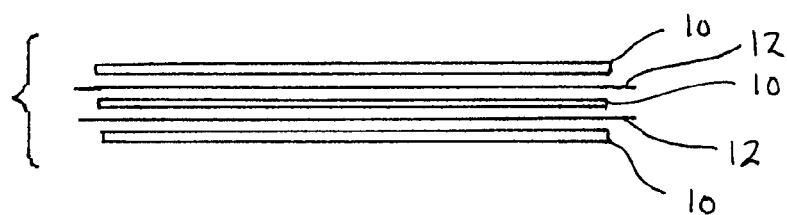
FIG. 1 is an exploded end view of material for use in fabricating a silicone dental arch appliance.
Figure 5:
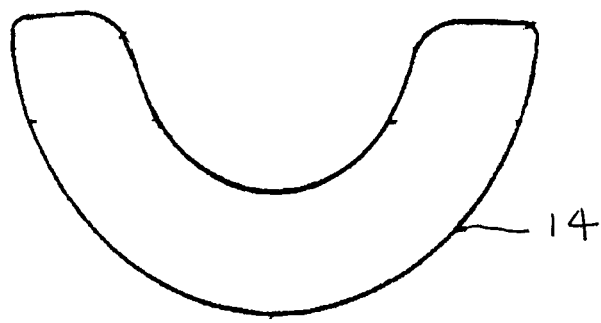
FIG. 5 is a plan view showing one alternate shape for material used to fabricate an appliance.

FIG. 1 shows a stack of individual silicone sheets 10 with consecutive sheets in the stack separated from an immediately overlying or underlying sheet by a release medium 12 which may be a sheet of suitable release material or a liquid medium applied to a sheet. Sheets 10 have identical rectangular shapes and the same thickness, but different shapes and thicknesses may also be used, such as the arch-shaped sheet 14 shown in FIG. 5. Applicant considers a sheet which is thinner than 1/16 inch too thin and a sheet which is thicker than 1/2 inch too thick. 1/4 inch thickness is well-suited for most uses.

Each sheet is pliable and capable of being shaped without spring-back onto a dental arch model 16 as will subsequently be explained with reference to FIGS. 2 and 3. Each sheet also contains a hibernating catalyst which when awakened by an activation process after the sheet has been shaped over a dental arch model, cures the shaped silicone material to capture a desired arch impression and desired final shape for the appliance as will be further explained hereinafter.

As explained earlier, silicone is cured either by tin catalyzation or by platinum catalyzation. In one form of the disclosed fabrication process, tin catalyzation is used. In another form, platinum catalyzation is used.

Figure 2:
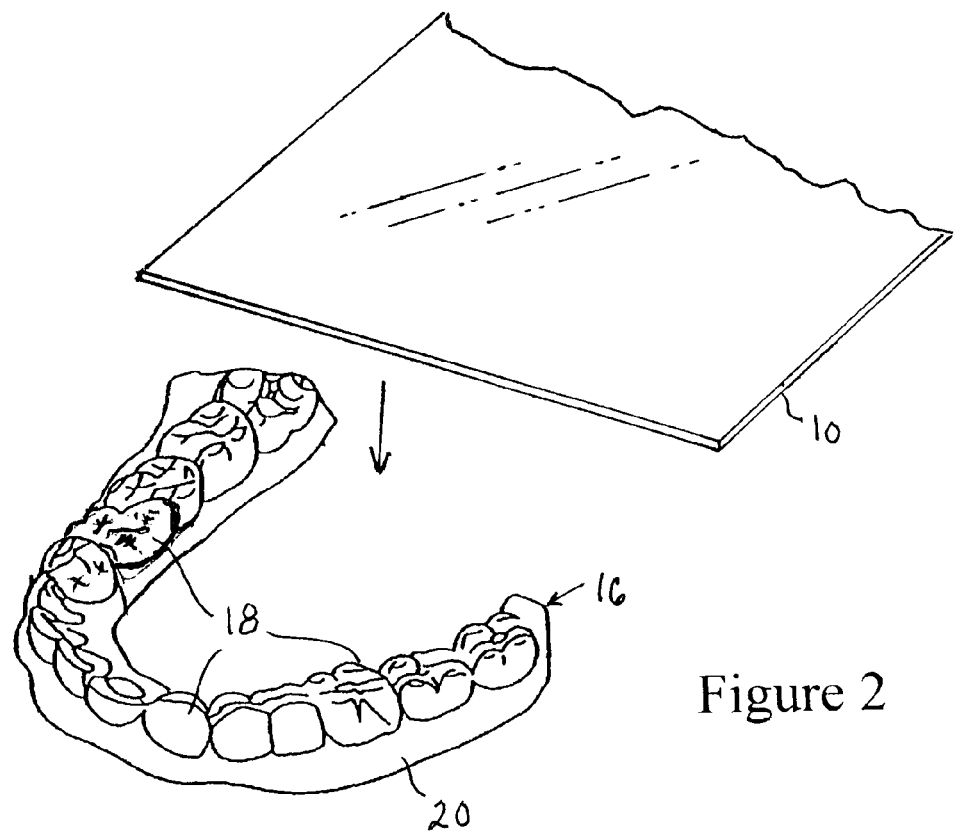
FIG. 2 is an exploded perspective view showing a start of an appliance fabrication process using some of the material shown in FIG. 1.
Figure 3:
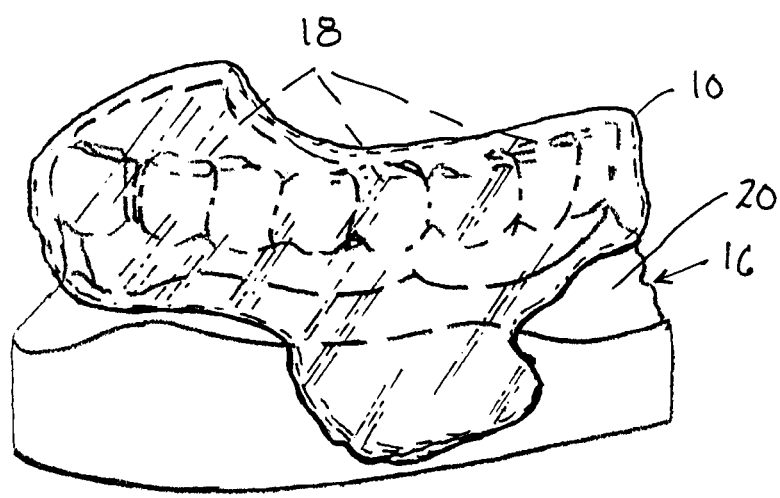
FIG. 3 is a perspective view showing a further stage of the fabrication process.
Figure 4:
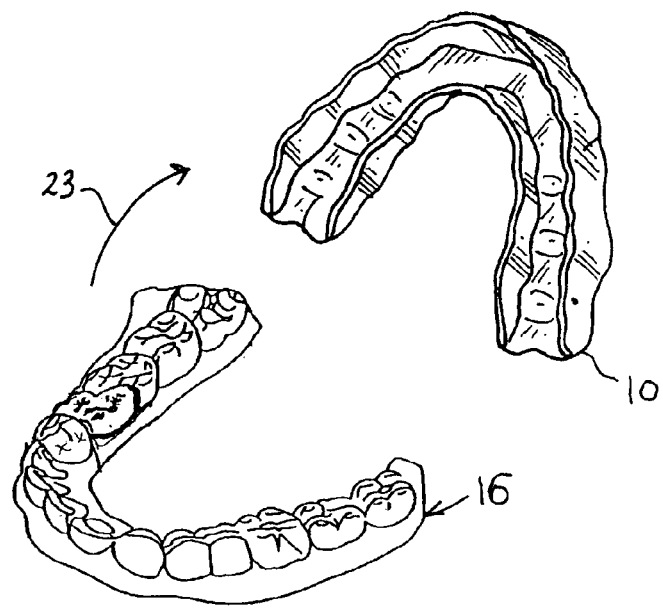
FIG. 4 is a perspective view showing a later stage of the fabrication process.

FIGS. 2-4 are illustrative of both processes. A sheet 10, or multiple sheets if greater thickness is desired, is placed over and onto teeth 18 and gum 20 of dental arch model 16. The shapeable material is worked onto the model to capture appropriate detail of the model, including minute detail when required, such as individual tooth detail, a well-defined gum line, and interstices between teeth.

FIG. 3 shows a condition where unactivated silicone which has been worked to capture the fine detail of teeth and gum happens to present an exterior shape on arch model 16 which would not be appropriate for a finished product because material is present below the gum 20. Because the shaped material is still uncured, that material may be displaced and/or removed to give the product a desired final shape as shown in FIG. 4 where the silicone formed from one or more sheets 10 is shown removed from arch model 16 strictly for the purpose of illustration.

Once the fabricator is satisfied with his/her work in capturing the arch impression and final shape, activation of the catalyst is triggered to cure the material.

Figure 7:
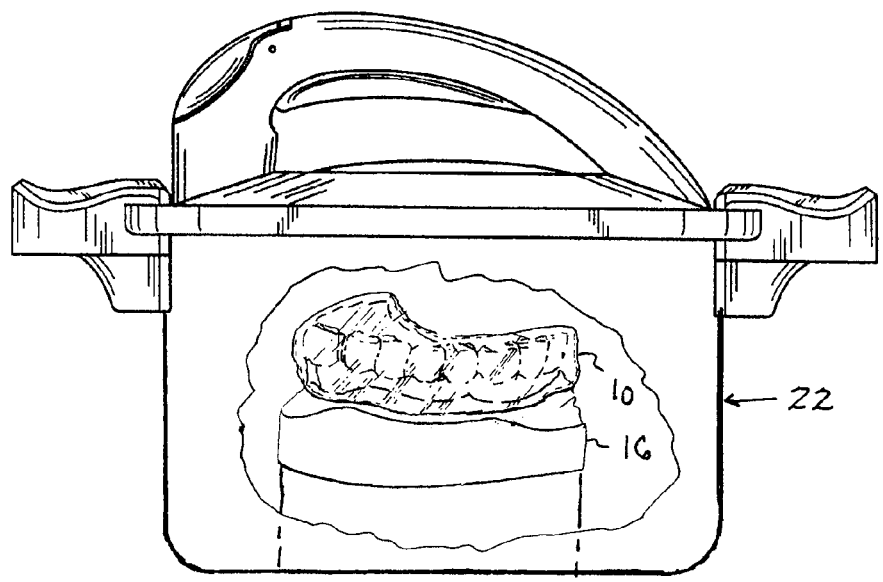
FIG. 7 is a view of equipment which can be used in one form of the fabrication process.

If the embedded catalyst is tin-based, arch model 16 with the formed silicone on it is placed in a moist environment to cure the material. If air bubbles are present in the formed silicone, it may be placed in a pot 22 shown in FIG. 7 which can function as a pressure pot before being placed in a moist environment. The pot can also be used to provide the moist environment by placing the arch model and worked silicone inside and covering the pot.

If the embedded catalyst is platinum-based, heat is applied to the silicone on the model, such as by placing the model with the formed silicone on it in pot 22 and then heating the pot, to cure the material. If air bubbles are present in the silicone, they may be removed by pressure either before or during heating. FIG. 4 also shows silicone 10 as the shape of the finished appliance after curing, as suggested by the arrow 23 indicating that the finished appliance has actually been removed from arch model 16. The catalyst and silicone are heated to a temperature of at least 300 degrees F. to achieve curing within an acceptable length of time.

Figure 8:
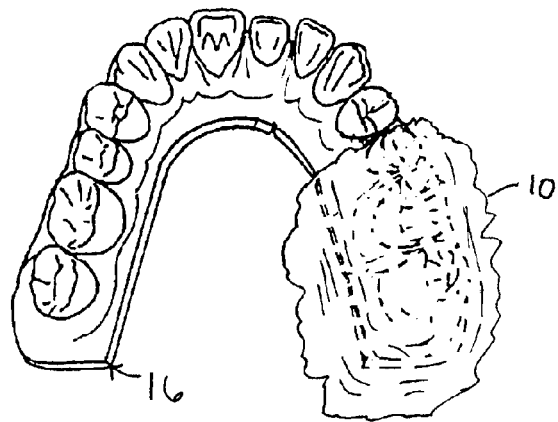
FIG. 8 is a plan view showing an alternate embodiment during a stage of the fabrication process.

FIG. 8 shows that silicone 10 may be applied to only a portion of a dental arch model 16 rather than the entire arch model.

The sheet form of silicone shown in previous Figures containing a hibernating catalyst is advantageous because that is a convenient way to select thickness. For example if each sheet is 0.125 inch thick, multiples of that thickness may be used to fabricate an appliance by selecting the appropriate number of sheets.

Figure 6:
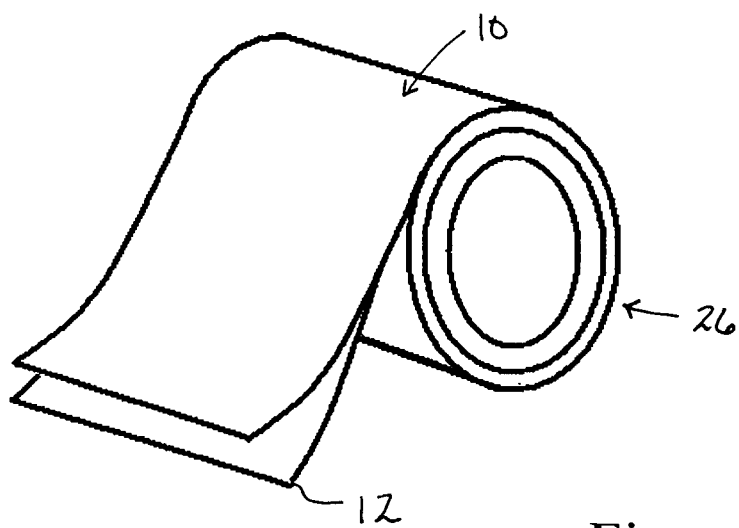
FIG. 6 is a perspective view showing another alternate shape for material used to fabricate an appliance.

Uncured silicone containing hibernating catalyst can be manufactured in other than the disclosed individual stacked sheet form shown in FIG. 1. FIG. 6 shows a coil or roll 26 formed from a length of uncured silicone 10 within which a hibernating catalyst is embedded. The silicone can be unrolled from the coil and cut to a desired length. The length of flat silicone is overlaid by a length of a release medium 12. Coil 26 is created by coiling the two parts 10, 12 into convolutions with release medium 12 separating each convolution of silicone from an immediately surrounding convolution.

The silicone can have some degree of optical transparency which allows a color to be imparted to an appliance by placing a colored material between two sheets prior to placement on a dental arch model. The colored material may be applied in liquid form and allowed to dry.

Regardless of the particular form in which silicone containing a hibernating catalyst is manufactured for sale to dentists and dental laboratories, the material is packaged to avoid unintentional or inadvertent activation of the catalyst. Because tin-catalyzed silicone can begin to very slowly cure at room temperatures, it is preferably packaged in a hermetically sealed enclosure and stored at room temperature or less than room temperature, such as in a refrigerator or freezer. Because platinum-catalyzed silicone requires elevated temperatures to cure, it may be stored at room temperature, but preferably is also stored under refrigeration. The specific manner in which both tin-catalyzed and platinum-catalyzed silicone are packaged and stored for subsequent use, determines their useful shelf life.

The disclosed processes can be used to fabricate various types of dental arch appliances which contain an element or elements other than just silicone.

Figure 9:
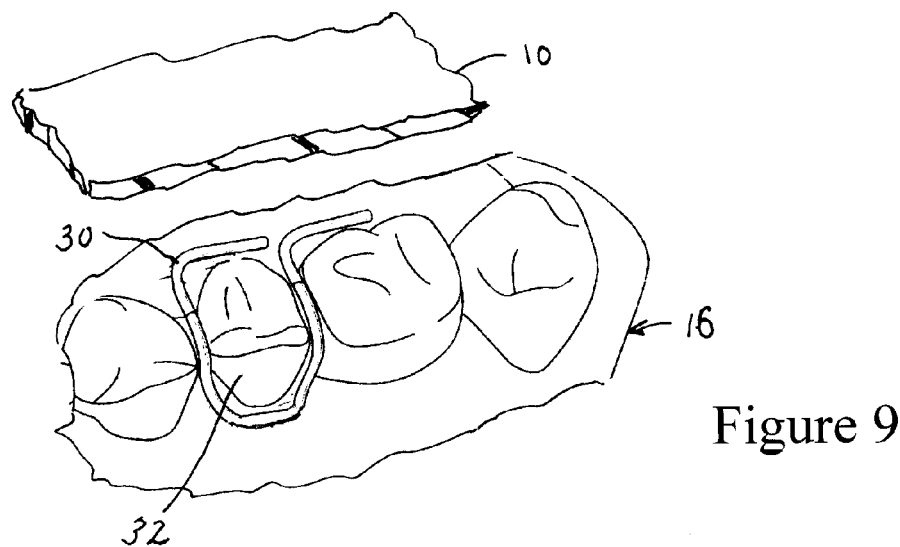
FIG. 9 is an exploded fragmentary perspective view of a modification.

FIG. 9 shows an example where a clasp 30 is fit to a tooth 32 of arch model 16 prior to forming a sheet 10 of uncured silicone over it. When the hibernating catalyst is awakened to cure the silicone, and after the silicone has cured, the clasp is embedded in the cured silicone and will come off tooth 32 when the finished appliance is removed from the arch model.

Figure 10:
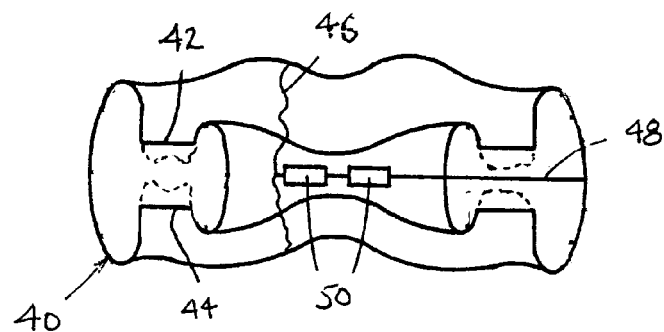
FIG. 10 is a rear view of another appliance.

FIG. 10 shows a mouthguard 40 having an upper arch impression 42 and a lower arch impression 44. The portion to the right of a break line 46 serves to explain the fabrication process while the portion to the left shows the finished product. One or more uncured silicone sheets 10 are used to fabricate the upper portion of the mouthguard, and one or more uncured sheets 10 are used to form the lower portion. The sheets are worked onto upper and lower dental arch models, as explained earlier. The models are then placed in registration to merge the worked silicone on each arch model along abutting surfaces 48. The merged silicones are then further worked to create air passages 50 in any desired number and locations which pass between labial and lingual surfaces without interfering with the respective impressions 42, 44. For example, the passages may be created by forcing plugs through the silicone. The plugs can be left in place after final working of the silicone. The silicone can then be cured, as described earlier, to unite the portions on the respective arch models so that when the arch models are removed, a mouthguard having both upper and lower arch impressions remains.

Alternately, air passages 50 could be created by working an uncured silicone sheet 10 on one arch model, placing plugs on the worked sheet, and then working a further sheet over the prior one to capture the plugs between then, and then registering that arch model with the other.

Coloring may be added to any appliance by applying a colorant to one side of an uncured silicone sheet and then covering the colorant with a second sheet. This can be done either while a sheet is flat or after it has been worked onto an arch model.

What is claimed is:

1. A method of enabling a silicone dental arch appliance which fits over one or more teeth of a person's dental arch to be fabricated by an end user of a commercial product comprising a mixture of uncured silicone and a hibernating tin-base catalyst which will awaken in response to an external influence effective to cause the uncured silicone to begin curing by catalytic action, the method comprising:

manufacturing a mixture of uncured silicone and a hibernating tin-based catalyst;

after the mixture has been manufactured, enclosing the mixture within a hermetically sealed enclosure to create a commercial product;

then shipping the commercial product from the manufacturer to an end user;

then, at the end user, opening the enclosure, removing the mixture, and working the mixture onto a dental arch model of a person's dental arch to capture in the worked mixture, an impression of one or more teeth of the dental arch model;

removing unwanted mixture from the worked mixture while leaving worked mixture containing the impression on the dental arch model; and then exposing the dental arch model with the worked mixture on it to an atmosphere whose relatively humidity is high enough to awaken the catalyst and cause the uncured silicone to begin to cure by catalytic action.

2. A method as set forth in claim 1 further comprising, prior to curing of the silicone, applying a colorant to an external surface of the uncured silicone, and then covering the colorant with more uncured silicone.

3. A method as set forth in claim 1 in which manufacturing a mixture of uncured silicone and a hibernating catalyst comprises manufacturing the mixture in sheet form having a thickness greater than 1/16 inch but less than 1/2 inch.

4. A method as set forth in claim 1 including forming air passages between labial and lingual surfaces of the mixture on the dental arch model prior to curing.

5. A method as set forth in claim 1 in which manufacturing a mixture of uncured silicone and a hibernating catalyst comprises manufacturing a stack of individual sheets of uncured silicone and hibernating catalyst with a release medium separating each sheet from an immediately overlying or underlying sheet.

6. A method as set forth in claim 1 in which manufacturing a mixture of uncured silicone and a hibernating catalyst comprises manufacturing a length of flat uncured silicone and hibernating catalyst as a coil containing convolutions with a release medium separating each convolution from an immediately surrounding convolution.

7. A method as set forth in claim 1 in which exposing the dental arch model with the worked mixture on it to an atmosphere whose relatively humidity is high enough to awaken the catalyst and cause the uncured silicone to begin to cure by catalytic action comprises placing the dental arch model with the worked mixture on it within a container having an interior containing an atmosphere whose relatively humidity is high enough to awaken the catalyst and cause the uncured silicone to begin to cure by catalytic action.

8. A method of enabling a silicone dental arch appliance which fits over one or more teeth of a person's dental arch to be fabricated by an end user of a commercial product comprising a mixture of uncured silicone and a hibernating catalyst which will awaken in response to an external influence effective to cause the uncured silicone to begin curing by catalytic action, the method comprising:

- manufacturing a mixture of uncured silicone and a hibernating catalyst;
- after manufacture of the mixture, enclosing the mixture within a sealed enclosure to create a commercial product;
- then shipping the commercial product from the manufacturer to an end user;
- then, at the end user, opening the enclosure, removing the mixture, and working the mixture onto a dental arch model of a person's dental arch to capture in the worked mixture an impression of one or more teeth of the dental arch model;
- removing unwanted mixture from the worked mixture while leaving worked mixture containing the impression on the dental arch model; and
- then exposing the dental arch model with the worked mixture on it to an external influence which is effective to awaken the catalyst and cause the uncured silicone to begin to cure by catalytic action and create the appliance;
- in which the working of the mixture onto a dental arch model further comprises placing one or more non-silicone elements on the dental arch model and then covering at least a portion of at least one of the elements with uncured silicone during working of the uncured silicone onto the dental arch model to cause the at least one of the elements to become at least partially embedded in the cured silicone and come off the dental arch model with the appliance when the appliance is removed from the dental arch model.

9. A method of fabricating a silicone dental arch appliance which fits over one of more teeth of a person's dental arch and which has some degree of optical transparency, the method comprising:

- placing silicone which contains a hibernating catalyst over one or more teeth of a dental arch model of a person's dental arch and working the silicone to capture an impression of one or more teeth of the arch model in the silicone;
- removing unwanted silicone from worked silicone;
- awakening the catalyst to cause uncured silicone remaining on the model to begin to cure by exposing the uncured silicone to an external influence which is effective on the catalyst to cause the silicone to begin to cure by catalytic action; and
- further comprising, prior to curing of the silicone, applying a layer of a colorant to an external surface of the uncured silicone, and then covering the colorant with more uncured silicone;
- in which applying a layer of a colorant to an external surface of the silicone comprises applying a liquid colorant to an external surface of the uncured silicone and allowing the liquid colorant to dry.

\* \* \* \* \*